United States Patent [19]

Biagini et al.

[11] Patent Number: 5,808,013
[45] Date of Patent: Sep. 15, 1998

[54] PROCESS FOR THE PREPARATION OF N-ALKYL SUBSTITUTED METAL CARBAMATE SOLUTIONS AND THEIR USE

[75] Inventors: Paolo Biagini, Trecate; Gabriele Lugli, S. Donato Milanese; Fausto Calderazzo, Ghezzano; Daniela Belli Dell'Amico, Pisa; Alessandra Merigo, Querceta, all of Italy

[73] Assignee: Enichem S.p.A., Milan, Italy

[21] Appl. No.: 677,903

[22] Filed: Jul. 10, 1996

[30] Foreign Application Priority Data

Aug. 4, 1995 [IT] Italy ................................. 1733MI95A

[51] Int. Cl.$^6$ ................................. C07F 5/00; C07F 9/00; C07F 7/00; B01J 31/00
[52] U.S. Cl. ................................. 534/13; 534/16; 556/44; 556/50; 556/56; 556/63; 556/107; 556/116; 556/134; 556/136; 556/137; 556/148; 556/183; 556/420; 556/152; 502/162
[58] Field of Search .......................... 534/13, 16; 556/44, 556/50, 55, 56, 63, 107, 116, 134, 136, 137, 148, 183, 420; 502/162; 526/152

[56] References Cited

U.S. PATENT DOCUMENTS 1,983,041 12/1934 MacMullin et al. .................... 260/112

FOREIGN PATENT DOCUMENTS

| 0 088 377 | 9/1983 | European Pat. Off. . |
| 559289 A1 | 9/1993 | European Pat. Off. . |
| 25 55 630 | 6/1976 | Germany . |

OTHER PUBLICATIONS

Chemical Abstracts of Japan, vol. 124, No. 13, AN–175436, Mar. 25, 1996.

*Primary Examiner*—Porfirio Nazario-Gonzalez
*Attorney, Agent, or Firm*—Oblon, Spivak, McClelland, Maier & Neustadt, P.C.

[57] ABSTRACT

Process for the preparation of N-alkyl substituted metal carbamate solutions characterized in that a water solution of the salt of the metal of which the corresponding carbamate is to be obtained, is reacted with an organic solution, basically consisting of an aprotic solvent and a secondary amine, saturated with carbon dioxide.

The above solutions can be used as catalysts in polymerization reactions of unsaturated monomers or for supporting metals on inorganic oxides.

39 Claims, No Drawings

PROCESS FOR THE PREPARATION OF N-ALKYL SUBSTITUTED METAL CARBAMATE SOLUTIONS AND THEIR USE

The present invention relates to a process for the preparation of N-alkyl substituted metal carbamate solutions.

More specifically, the present invention relates to a process for the preparation of solutions of N-alkyl substituted metal carbamates, operating under non-anhydrous conditions, starting from water solutions of the salts of the metals of which the corresponding carbamate is to be obtained.

The present invention also relates to the use of these solutions as catalysts in polymerization reactions of unsaturated monomers or for supporting metals on inorganic oxides.

The synthesis of N-alkyl substituted metal carbamates having the following general formula:

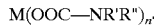

M(OOC—NR'R")$_{n'}$ wherein:
M represents a metal belonging to groups 2 to 14 of the periodic system;
R' and R", the same or different, represent organic radicals of the aliphatic, cycloaliphatic or aromatic type, containing from 1 to 20 carbon atoms;
n' is the valence of the metal;
is widely described in the known art.

For example, in "Journal of the Chemical Society" (1970), Part A, page 2250, G. Chandra et al. describe the preparation of titanium carbamate by reaction between the corresponding titanium amide and carbon dioxide. An analogous reaction is described by M. H. Chisholm et al., in "Journal of American Chemical Society" (1977), Vol. 99, page 782.

T. V. Ashwort et al. in "Journal of Organometal Chemistry" (1976), Vol. 121, page 58 and G. La Monica et al. in "Journal of Chemical Society. Chemical Communication" (1976), page 1777, describe the synthesis of metal carbamates starting from metal hydrides, amines and carbon dioxide.

Italian patent N. 1.038.285 describes the synthesis of metal carbamates, in particular uranium carbamates, by means of a process in which a metal halide is reacted, in an organic solvent, with an amine and carbon dioxide. An analogous method, in particular with respect to the synthesis of copper carbamates (II), is described by E. Agostinelli in "Gazzetta Chimica Italiana" (1988), Vol. 118, page 729.

In all the cases described above, however, it is necessary to start from derivatives of the metals which are not easy to prepare such as, for example, amides or alcoholates, or from anhydrous chlorides which are not normally available industrially for all metals. In addition, the synthesis conditions are such that water must be rigorously excluded during all the reaction phases.

It is therefore evident that there is no explanation in the known art of how to obtain metal carbamates starting from water solutions of the salts of the metals of which the corresponding carbamate is to be obtained. It is also evident that the syntheses described in the known art are particularly simple only if the salts of the starting metals are at least slightly soluble in the aprotic solvents in which the synthesis is carried out or, even better, when the salts of the metals have a strong covalent nature which makes them soluble even in hydrocarbon solvents. Examples of salts of metals soluble in hydrocarbon solvents are silicon chloride ($SiCl_4$), titanium chloride ($TiCl_4$), vanadium chloride ($VCl_4$), molibden chloride ($MoCl_5$)

The Applicant has now unexpectedly found that solutions of N-alkyl substituted metal carbamates can be prepared, operating under non-anhydrous conditions, starting from water solutions of the salts of the metals of which the corresponding carbamate is to be obtained, in spite of the well known sensitivity of these carbamates to water. This process enables the disadvantages of the known art to be overcome.

The present invention therefore relates to a process for the preparation of solutions of N-alkyl substituted metal carbamates having the following general formulae (I), (II), (III) and (IV):

$[M(OOC—NR_1R_2)_n]_w$ (I)

$[MO_x(OOC—NR_1R_2)_{n-2x}]_w$ (II)

$[M(L_1)_y(OOC—NR_1R_2)_n]_w$ (III)

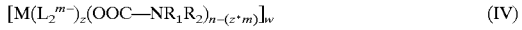

$[M(L_2^{m-})_z(OOC—NR_1R_2)_{n-(z \cdot m)}]_w$ (IV)

wherein:
M represents a metal belonging to groups 2 to 14 of the periodic system;
$L_1$ represents a neutral ligand;
$L_2^{m-}$ represents an anionic ligand having a negative charge;
$R_1$ and $R_2$, the same or different, represent an organic radical containing from 1 to 20 carbon atoms;
n represents the oxidation state of the metal M;
x represents an integer or fraction between 0.25 and n−1;
y represents an integer or fraction between 0.25 and 3;
z represents an integer or fraction between 0.25 and n−1;
w represents an integer within the range of 1 to 12;
m represents an integer between 1 and 3;
characterized in that a water solution of the salt of the metal of which the corresponding carbamate is to be obtained, is reacted with an organic solution basically consisting of an aprotic solvent and a secondary amine having general formula (V):

$NHR_1R_2$ (V)

wherein $R_1$ and $R_2$ have the same meaning defined above, saturated with carbon dioxide.

The organic radicals $R_1$ and $R_2$ in general formulae (I) to (IV) are preferably alkyl, cycloalkyl, aryl, arylalkyl or alkylaryl radicals. Organic radicals $R_1$ and $R_2$ having from 2 to 10 carbon atoms are particularly preferred.

Typical examples of organic radicals $R_1$ and $R_2$ are methyl, ethyl, propyl, n-butyl, isopropyl, isobutyl, n-hexyl, cyclohexyl, methylcyclohexyl, phenyl, benzyl, ethylphenyl, phenylethyl, xylyl, etc.

Typical examples of metals belonging to groups 2 to 14 of the periodic system which can be used for the purposes of the present invention are titanium, vanadium, chromium, iron, cobalt, nichel, copper, silver, zirconium, niobium, neodymium, dysprosium, gadolinium, samarium, praseodymium, uranium, etc. The above metals can be in any of their different oxidation states.

Typical examples of neutral ligands $L_1$ useful for the purpose of the present invention are amines or organic phosphines, organic nitriles or any other neutral molecule capable of binding itself to the metal M with a co-ordination bond without jeopardizing the stability of the carbamate itself. Preferred neutral ligands $L_1$ are amines and organic nitriles.

Typical examples of anionic ligands $L_2^{m-}$ are halides, nitrates, sulfates, acetates and the like. Preferred anionic $L_2^{m-}$ ligands are halides, sulfates, acetates.

The values which the indexes n, x, y, z, w and m can have in the above general formulae (I), (II), (III) and (IV) are selected within the ranges specified above depending on the nature of the metal M, the ligands $L_1$ and $L_2^{m-}$ and the radicals $R_1$ and $R_2$.

Metal salts useful for the purpose of the present invention are salts of metals formed from mineral acids such as, for example, halides, sulfates, phosphates, etc., or from organic acids such as, for example, acetates, formiates, propionates, etc. These salts must be soluble in water and must not cause decomposition or strong hydrolysis reactions leading to the formation of insoluble products.

Typical examples of metal salts which can be used are titanium chloride ($TiCl_3$), chromium chloride ($CrCl_2$), ferrous chloride ($FeCl_2$), ferric chloride ($FeCl_3$), cobalt chloride ($CoCl_2$), nichel chloride ($NiCl_2$), copper acetate ($Cu(CH_3COO)_2$), $LnCl_3$ wherein Ln represents a lanthanide i.e. a metal with an atomic number of between 57 and 71 such as, for example, neodymium or praseodymium, $AcCl_4$ wherein Ac represents an actinide i.e. a metal with an atomic number of between 89 and 103 such as, for example, thorium or uranium, etc. These salts can also be used in their hydrate forms.

Aprotic solvents useful for the purposes of the present invention are aliphatic hydrocarbons such as, for example, pentane, hexane, octane, decane, etc.; chlorinated aliphatic hydrocarbons such as methylene chloride, etc.; aromatic hydrocarbons such as, for example, benzene or toluene, etc.; ethers such as diethyl ether, etc. A mixture of two or more of the above solvents can also be used.

Preferred aprotic solvents are hexane, methylene chloride, diethyl ether.

Secondary amines having general formula (V) useful for the purposes of the present invention are diethylamine, di-n-propylamine, di-isopropylamine, di-n-butyl amine, di-sec-butylamine, di-n-pentylamine, di-n-hexyl amine, di-cyclohexylamine, etc.

Preferred amines are di-n-propylamine, di-n-butyl amine.

The water solutions of the metal salts can be advantageously prepared with the various methods well known in the prior art as described, for example, in "Gmelin Handbuch der Anorganischen Chemie", Springer-Verlag Ed. (Berlin-Heidelberg-New York), in the volumes relating to metals considered each time. Among the methods described therein, one of the simplest and industrially most interesting is that relating to the production of water solutions of metal salts by reacting the oxide of the metal of interest with water solutions of mineral or organic acids generating the corresponding inorganic or organic salt in solution.

The water solutions of the metal salts can also be prepared by dissolving the salt directly in water, when the salt is easily available on the market.

Since, as already mentioned above, the only restriction to be respected is that the starting metal salt selected is stable in a water solution and does not give rise to insoluble total hydrolysis products, experts in the field can identify the most convenient method for obtaining the above water solutions without any limitation or improvement of the present invention.

A general description follows of the process of the present invention.

For this purpose, the water solution of the selected metal salt is prepared at a concentration of between $10^{-2}M$ and $10^1M$, preferably between $10^{-1}M$ and 1M, depending on the type of salt and metal. For example, 5.0 mmoles of the selected metal salt are dissolved in 10 $cm^3$ of water and brought to a temperature of between $-5°$ C. and $+25°$ C., preferably $0°$ C.

A second solution is then prepared by dissolving a secondary amine having general formula (V) in an aprotic solvent such as, for example, hexane, so as to obtain a concentration of the amine of between $10^{-1}M$ and 1M. For example, from 20 to 100 mmoles of a secondary amine having general formula (V), are dissolved in 100–150 ml of an aprotic solvent and brought to a temperature of between $-15°$ C. and $+25°$ C., preferably between $-15°$ C. and $0°$ C. This solution is then saturated with carbon dioxide by bubbling the gas through a glass tube immersed in the solution of amine and terminating with a porous glass septum to help the dispersion and dissolution of the gas in the solution which is maintained at a temperature of between $-15°$ C. and $+25°$ C., preferably between $-15°$ C. and $0°$ C. The saturation operation requires short times, generally of between 10 and 15 minutes.

At the end of the saturation, the water solution of the metal salt prepared as described above is added to the solution of the secondary amine. In this way two phases are formed (water/organic) which are maintained in contact by light stirring for the desired time, generally between a few minutes and several days, the solution being maintained at the preset temperature, generally between $-15°$ C. and $+25°$ C., preferably between $-15°$ C. and $0°$ C.

The molar ratio between the metal salt and the amine used in the reaction can vary within a wide range. The lower value however will never be less than n (where n represents the oxidation state of the metal M), whereas the higher value will depend on the type of metal used. Preferred values are those between 2 and 15.

The organic phase can subsequently be separated from the water phase using methods known in the art such as, for example, by separation funnel, decanting or centrifugation, ensuring that the operating temperature is between $-15°$ C. and $+25°$ C.

In some cases, depending on the type of metal used, the mixture consisting of the two water/organic phases, is placed in a cold bath, generally at a temperature of between $-30°$ C. and $-20°$ C., and in a few minutes is able to freeze the water phase thus allowing the separation of the organic phase at a low temperature, for example by siphoning.

The organic phase, after separation from the water phase, is dried, for example on dry anhydrous sulfate and analyzed to quantify the content of metal carbamate. This phase, in fact, contains the N-alkylcarbamate having general formula (I) or (II) or (III) or (IV) of the metal selected, with yields ranging from 30% to 90%. The yields are calculated on the quantity of metal reacted as a salt in the water solution.

The process of the present invention is generally carried out in air. However, in some specific cases, it must be conducted under a nitrogen stream, using the well-known vacuum-nitrogen technique, to avoid oxidation processes of the metal ion.

The possibility of obtaining N-alkylcarbamates having general formula (I) or (II) or (III) or (IV), depends on the type of aprotic solvent and metal used. In fact, for example, using solvents with higher water saturation values and/or extending the contact time between the water phase and the organic phase it is possible, depending on the type of metal used, to obtain oxocarbamates having general formula (II) whereas, with solvents having low water saturation values, a temperature of 0° C. and contact times of less than three minutes, it is possible to obtain carbamates having general formula (I).

The type of secondary amine having general formula (V) used, also influences the reaction and the nature of the end-product. For example, di-n-butylamine gives carbamates having a higher solubility in aliphatic hydrocarbons with respect to di-ethylamine. Moreover, the type of amine used can favour the production of N-alkyl substituted metal carbamates having general formula (III) rather than (I) or (II).

The Applicant has surprisingly found that the solutions of N-alkyl substituted metal carbamates having general formula (I), (II) (III) and (IV) obtained with the process of the present invention can be used, as catalysts, in polymerization reactions of unsaturated monomers.

A further object of the present invention therefore relates to the use of solutions of N-alkyl substituted metal carbamates having general formula (I), (II), (III) and (IV), as catalysts, in polymerization reactions of unsaturated monomers.

Unsaturated monomers which can be polymerized using the above solutions are olefinic monomers such as, for example, ethylene, propylene, butene-1, hexene, octene, styrene, etc.; or diolefinic monomers such as, for example, butadiene, isoprene, 1,3-pentadiene, etc.

The use of the N-alkyl metal carbamate solutions obtained with the process of the present invention depends, as described in the known art, on the type of unsaturated monomer to be used. For example, metal carbamates belonging to group 4 such as, for example, titanium or zirconium, or group V such as, for example, vanadium or niobium, are particularly suitable for the polymerization of olefins (ethylene, propylene, etc.); metal carbamates belonging to group 9 such as, for example, cobalt, or group 10 such as, for example, nichel, or group 3 such as, for example, neodymium, are particularly suitable for the polymerization of di-olefins (butadiene, isoprene, 1,3-pentadiene, etc.).

A process is described for the polymerization of butadiene using a solution of a catalyst based on neodymium carbamate obtained with the process of the present invention.

The catalytic solution is prepared by operating according to the well-known preformation technique. All operations relating to the preparation of the catalytic mixture and polymerization test are carried out with the rigorous exclusion of oxygen and humidity using the well-known vacuum-nitrogen method and using anhydrous solvents. These operating conditions, as well as the polymerization procedure are well-known to experts in Ziegler-Natta polymerization techniques.

The solution of catalyst is prepared by introducing 6 ml ($0.66 \times 10^{-3}$ gram/atoms of Nd) of a water solution of neodymium carbamate prepared according to the process of the present invention and 26.4 ml ($13.2 \times 10^{-3}$ moles) of a 0.5M solution of aluminium di-isobutylmonohydride into a Schlek tube. The mixture is cooled to 0° C. for 1 hour under stirring. 1.98 ml ($1.98 \times 10^{-3}$ moles) of a 1M hexane solution of t-butylchloride are then added and the mixture is left under stirring for 18 hours at room temperature. The catalytic mixture obtained contains $1.92 \times 10^{-5}$ gram/atoms of neodymium per ml.

The polymerization reaction is carried out in a drinking bottle by charging, in the order, 150 ml of hexane, 15 g of butadiene monomer and 2 ml of the catalytic mixture previously prepared. After maintaining the bottle at 50° C. for 2 hours, the polymer is recovered by pouring the contents of the bottle in methanol and drying the coagulated polymer in a vacuum oven. 7.5 g (50% yield) of elastomeric polymer are recovered which, on infra-red analysis, proves to contain 98.4% of chained 1,4-cis units.

Italian patent application N.MI92A 00416 describes a process for supporting one or more metals on a matrix based on one or more oxides, comprising the contact of said matrix, in a medium consisting of an aprotic organic solvent, with one or more N-alkyl substituted metal carbamates. In this case, the solutions of metal carbamates are prepared under strictly anhydrous conditions.

The Applicant has now found that the solutions of N-alkyl substituted metal carbamates having general formula (I), (II), (III) and (IV) obtained with the process of the present invention, can be used for supporting metals on a matrix based on oxides.

A further object of the present invention therefore relates to a process for supporting one or more metals on a matrix based on one or more oxides comprising the contact of said matrix with a solution of N-alkyl substituted metal carbamate characterized in that said solution has been obtained starting from a water solution of the metal salt of which the corresponding carbamate is to be obtained.

Matrices based on oxides useful for the purpose are those described in Italian patent application N.MI92A 00416. Typical examples of the above matrices are silica, alumina, magnesium oxides etc.

A process is described for the supporting of neodymium carbamate on a silica carrier.

A hexane solution of neodymium carbamate is prepared as described above and contains $0.17 \times 10^{-3}$ gram/atoms of neodymium per ml.

29.4 ml ($4.23 \times 10^{-3}$ gram/atoms of Nd) of the above solution are evaporated under a mechanical pump vacuum (1.33 Pa), at room temperature. The residue is in the form of a slightly pink/pale-blue coloured solid. Operating under a dry nitrogen stream to keep the reagents at atmospheric humidity, 100 ml of heptane are added to the solid residue together with 12.5 g of commercial silica of the type Grace 3216/30 are added. As it has been found that the quantity of metal chemically fixed to the carrier is proportional to the equivalents of hydroxyls present in the silica structure, the silica is released from the water absorbed by drying at 180° C. under vacuum (1.33 Pa), before the reaction with the carbamate solution. After this treatment the silica used (of the type Grace 3216/30) contains a content of hydroxyls equal to $2.4 \times 10^{-3}$ equivalents per gram of silica.

The suspension of silica in the heptane solution of the carbamate is maintained under mechanical stirring, at room temperature, for 72 hours after which the decolouring of the heptane phase, previously light-blue and the colouring of the silica to light blue, are observed. The heptane layer is then removed by filtration, the solid dried under vacuum (1.33 Pa) at room temperature and analyzed for the content of neodymium which proves to be $2.2 \times 10^{-3}$ equivalents of neodymium per gram of silica.

An analogous procedure can be used for other inorganic carriers such as alumina, magnesium oxide and others. Experts in the art can treat these carriers as in the case of silica to make them suitable for supporting metal carbamates in solution, obtained by the process of the present invention.

The carriers containing metal carbamates chemically linked to the silica structure can be advantageously used for the preparation of catalytic systems to be used in the polymerization in heterogeneous phase of monolefins and diolefins using the techniques well known in the art. Also in this case, as already described above for the preparation of solutions of N-alkyl substituted metal carbamates to be used as catalysts in the homogeneous polymerization of unsaturated monomers, the known art can suggest which particular carriers and metals are preferable for the specific polymerization of certain monomers.

The following examples are provided for a better illustration of the present invention and for its embodiment but do not limit the scope of the invention in any way.

EXAMPLE 1

Preparation of a Hexane Solution of Neodymium Carbamate Having the Formula $Nd(O_2CNBu_2)_3$ 1.0 g ($5.9 \times 10^{-3}$ gram/atoms of Nd) of neodymium oxide ($Nd_2O_3$) is suspsended in 15 ml of water containing $17.7 \times 10^{-3}$ equivalents of HCl. The suspension is stirred at 40° C. for 20 minutes obtaining the complete dissolution of the neodymium oxide. The clear solution thus obtained, containing neodymium trichloride ($NdCl_3$) is cooled to 0° C.

150 ml of hexane are added, in a 250 ml flask, to 10 ml ($58.9 \times 10^{-3}$ moles) of di-n-butylamine, cooled to −15° C. and saturated with carbon dioxide by bubbling the gas through a glass tube equipped at the end with a porous septum immersed in the hexane solution. After 15 minutes of bubbling the tube is removed, the solution is left to rise to 0° C. and the water solution of neodymium trichloride ($NdCl_3$) cooled to 0° C. is added. The mixture of the two phases (water/organic) is maintained under light stirring, at 0° C., for 2 minutes during which there is the complete decolouring of the water phase, whereas the organic phase becomes light blue.

The flask containing the mixture is placed in a cold bath (−25° C.) which causes the rapid solidification of the water layer. The hexane layer is then separated by siphoning, 2.0 g of sodium sulfate are added and the mixture is left to rest for a few hours. The solution is then separated from the sodium sulfate and evaporated at reduced pressure (1.33 Pa) recovering 3.4 g of a pink-light blue solid corresponding to $Nd(O_2CNBu_2)_3$, having a content of neodymium of 21.5% and carbon dioxide of 19.5% [calculated for $Nd(O_2CNBu_2)_3$: Nd=21.8% and $CO_2$=20.0%]. The yield, calculated on the neodymium used for the reaction, proves to be 86%.

EXAMPLE 2

Preparation of a Hexane Solution of Praseodymium Carbamate Having the Minimum Formula $Pr_2(O)(O_2CNBu_2)_4$ Following the same operating procedure as in example 1, 1.6 g ($4.5 \times 10^{-3}$ gram/atoms of Pr) of praseodymium trichloride hydrate ($PrCl_3.6H_2O$) are suspended in 15 ml of water and the solution is cooled to 0° C. The solution thus obtained is added to 100 ml of hexane containing 5.4 ml ($31.8 \times 10^{-3}$ moles) of di-n-butylamine saturated at 0° C. with carbon dioxide.

The two phase mixture (water/organic) is maintained under light stirring for 10 minutes at 0° C.

The hexane phase is then separated from the frozen water phase. From evaporation of the hexane 1.5 g of a solid are recovered corresponding to $Pr_2(O)(O_2CNBu_2)_4$, having a content of praseodymium of 28.9% [calculated for $Pr_2(O)(O_2CNBu_2)_4$: Pr=28.6%]. The yield, calculated on the praseodymium used for the reaction, is 68%.

EXAMPLE 3

Preparation of a Hexane Solution of Holmium Carbamate Having the Minimum Formula $Ho_2(O)_2(O_2CNBu_2)_2$ Following the same operating procedure as in example 1, 0.96 g ($5.07 \times 10^{-3}$ gram/atoms of Ho) of holmium oxide ($Ho_2O_3$) are suspended in 15 ml of water containing $15.2 \times 10^{-3}$ equivalents of HCl. The solution, after cooling to 0° C., is added to 100 ml of hexane containing 6.1 ml ($36 \times 10^{-3}$ moles) of di-n-butylamine saturated at 0° C. with carbon dioxide.

The two phase mixture (water/organic) is maintained under light stirring for 30 minutes at 0° C.

The hexane phase is then separated from the frozen water phase. From evaporation of the hexane 0.92 g of a solid are recovered corresponding to $Ho_2(O)_2(O_2CNBu_2)_2$, having a content of holmium of 41.0% and of $CO_2$ of 13.5% The yield, calculated on the holmium used for the reaction, is 45%.

EXAMPLE 4

Preparation of a Heptane Solution of Copper Carbamate Having the Formula $Cu(NHPr_2)_2(OCONPr_2)_2$ Following the same operating procedure as in example 1, 1.11 g ($6.5 \times 10^{-3}$ gram/atoms of Cu) of copper chloride hydrate ($CuCl_2.2H_2O$) are suspended in 20 ml of water and the solution is maintained at room temperature. The solution is added to 100 ml of heptane containing 8.9 ml ($65 \times 10^{-3}$ moles) of di-n-propylamine saturated, at room temperature, with carbon dioxide.

The two phase mixture (water/organic) is maintained under light stirring for 48 hours at room temperature.

The heptane phase is then separated from the water phase by means of a separation funnel, dried on 2.0 g of sodium sulfate and then evaporated at room temperature with a vacuum pump (1.33 Pa). From evaporation of the heptane 2.9 g of a solid are recovered corresponding to $Cu(NHPr_2)_2(OCONPr_2)_2$, having a content of copper of 10.8% [calculated for $Cu(NHPr_2)_2(OCONPr_2)_2$: Cu=11.5%]. The yield, calculated on the copper used for the reaction, is 76%.

EXAMPLE 5

Preparation of a Heptane Solution of Cobalt Carbamate Having the Formula $Co(OCONBu_2)_2$ Following the same operating procedure as in example 1, 1.36 g ($5.7 \times 10^{-3}$ gram/atoms of Co) of cobalt chloride hydrate ($CoCl_2.6H_2O$) are suspended in 30 ml of water and the solution is cooled to 0° C. The solution is added to 100 ml of heptane containing 9.7 ml ($57.1 \times 10^{-3}$ moles) of di-n-butylamine saturated, at 0° C., with carbon dioxide.

The two phase mixture (water/organic) is maintained under light stirring for 3 minutes at 0° C.

The heptane phase is then separated from the water phase by means of a separation funnel, dried on 2.0 g of sodium sulfate and then evaporated at room temperature with a vacuum pump (1.33 Pa). From evaporation of the heptane 1.72 g of a solid are recovered corresponding to $Co(OCONBu_2)_2$, having a content of cobalt of 14.9% [calculated for $Co(OCONBu_2)_2$: Co=14.6%]. The yield, calculated on the cobalt used for the reaction, is 76%.

EXAMPLE 6

Preparation of a Heptane Solution of Nichel Carbamate Having the Formula $Ni(OCONBu_2)_2$ Following the same operating procedure as in example 5, 1.12 g ($4.7 \times 10^{-3}$ gram/atoms of Ni) of nichel chloride hydrate ($NiCl_2.6H_2O$) are suspended in 10 ml of water and the solution is cooled to 0° C. The solution is added to 100 ml of heptane containing 9.0 ml ($53 \times 10^{-3}$ moles) of di-n-butylamine saturated, at 0° C., with carbon dioxide.

The two phase mixture (water/organic) is maintained under light stirring for 3 minutes at 0C.

The heptane phase is then separated from the water phase by means of a separation funnel, dried on 2.0 g of sodium sulfate and then evaporated at room temperature with a vacuum pump (1.33 Pa). From evaporation of the heptane 1.2 g of a solid are recovered corresponding to $Ni(OCONBu_2)_2$, having a content of nichel of 15.0% [calculated for $Ni(OCONBu_2)_2$: Ni=14.6%]. The yield, calculated on the nichel used for the reaction, is 65%.

EXAMPLE 7

Preparation of a Heptane Solution of Uranium Carbamate Having the Minimum Formula $U_2(O)(OCONBu_2)_6$ Following the same operating procedure as in example 1, 2.8 g ($7.3 \times 10^{-3}$ gram/atoms of U) of uranium chloride ($UCl_4$) are suspended in 20 ml of water and the solution is cooled to 0° C. The solution is added to 100 ml of heptane containing 12.4 ml ($73.0 \times 10^{-3}$ moles) of di-n-butylamine saturated, at 0° C., with carbon dioxide.

The two phase mixture (water/organic) is maintained under light stirring for 30 minutes at 0° C.

The heptane phase is then separated from the water phase by means of a separation funnel, dried on 2.0 g of sodium sulfate and then evaporated at room temperature with a vacuum pump (1.33 Pa). From evaporation of the heptane 3.9 g of a green-coloured solid are recovered corresponding to $U_2(O)(OCONBu_2)_6$, having a content of uranium of 30.5% [calculated for $U_2(O)(OCONBu_2)_6$: U=31.2%]. The yield, calculated on the uranium used for the reaction, is 68%.

EXAMPLE 8

Preparation of a Toluene Solution of Chromium Carbamate Having the Formula $Cr_2(NHBu_2)_2(OCONBu_2)_4$ All the operations are carried out under a nitrogen stream according to the well-known vacuum-nitrogen technique.

1.02 g ($8.3 \times 10^{-3}$ gram/atoms of Cr) of chromium chloride ($CrCl_2$) are charged into a 50 ml Schlenk test-tube containing 15 ml of deaerated water and the solution is cooled to 0° C.

100 ml of toluene and 4.0 ml ($23.6 \times 10^{-3}$ moles) of di-n-butylamine, saturated, are added, in order, to a second Schlenk test-tube, and the test-tube is then cooled in a bath to 0° C. A stream of carbon dioxide is passed through a glass tube ending with a porous septum immersed in the toluene solution until saturation. The water solution of chromium chloride is added to this solution.

The two phase mixture (water/organic) is maintained under light stirring for 5 minutes at 0° C.

The test-tube is then immersed in a cold bath at −20° C., the water layer is frozen and the toluene phase is recovered, dried on 2 g of sodium sulfate for 2 hours and then filtered. The filtrate is evaporated under vacuum (1.33 Pa) and 1.88 g of a reddish-black coloured solid are recovered corresponding to $Cr_2(NHBu_2)_2(OCONBu_2)_4$, having a content of chromium of 9.2% [calculated for $Cr_2(NHBu_2)_2(OCONBu_2)_4$: Cr=9.9%]. The yield, calculated on the chromium used in the reaction, is 40%.

EXAMPLE 9

Preparation of a Toluene Solution of Titanium Carbamate Having the Minimum Formula $Ti_3(O)(OCONBu_2)_7$ The same procedure is carried out as in example 8.

0.51 g ($3.31 \times 10^{-3}$ gram/atoms of Ti) of titanium chloride ($TiCl_3$) are charged into a 50 ml Schlenk test-tube containing 10 ml of deaerated water and the solution is cooled to 0° C.

100 ml of toluene and 10.0 ml ($58.9 \times 10^{-3}$ moles) of di-n-butylamine are added, in order, to a second Schlenk test-tube, and the test-tube is then cooled in a bath to 0° C. A stream of carbon dioxide is passed through a glass tube ending with a porous septum immersed in the toluene solution until saturation. The water solution of titanium chloride is added to this solution.

The two phase mixture (water/organic) is maintained under light stirring for 5 minutes at 0° C. A semisolid solution is formed which is left for 10 hours at room temperature. After this period the toluene layer becomes dark blue.

Still operating under nitrogen, the mixture is transferred to a glass centrifugation test-tube equipped with a cap. After centrifuging for 15 minutes, the upper toluene layer, which is intensely blue-coloured, is separated by siphoning and 2 g of sodium sulfate are added. After 2 hours the mixture is filtered and the solvent is eliminated by evaporation under vacuum (1.33 Pa).

0.7 g of a blue-black coloured solid are recovered having a content of titanium of 10.1% The yield, calculated on the titanium used in the reaction, is 42%.

We claim:

1. A process for preparing solutions of N-alkyl substituted metal carbamates having the following formulae (I), (II), (III) or (IV);

$$(M(OOC\text{—}NR_1R_2)_n)_w \qquad (I)$$

$$(MO_x(OOC\text{—}NR_1R_2)_{n-2x})_w \qquad (II)$$

$$(M(L_1)_y(OOC\text{—}NR_1R_2)_n)_w \qquad (III)$$

$$(M(L_2{}^{m-})_z(OOC\text{—}NR_1R_2)_{n-(z \cdot m)})_w \qquad (IV)$$

wherein:

M represents a metal belonging to groups 2 to 14 of the periodic system;

$L_1$ represents a neutral ligand;

$L_2{}^{m-}$ represents an anionic ligand having a negative charge;

$R_1$ and $R_2$, and the same or different, and each represents an organic radical containing from 1 to 20 carbon atoms;

n represents the oxidation state of the metal M;

x represents an integer or fraction between 0.25 and n−1;

y represents an integer or fraction between 0.25 and 3;

z represents an integer or fraction between 0.25 and n−1;

w represents an integer within the range of 1 to 12;

m represents an integer between 1 and 3;

which process comprises reacting a water solution of the salt of the metal from which the corresponding carbamate is to be obtained, with an organic solution consisting essentially of an aprotic solvent and a secondary amine, the secondary amine having the formula (V):

$NHR_1R_2$ (V)

wherein $R_1$ and $R_2$ have the same meaning defined above, with saturation by carbon dioxide.

2. The process according to claim 1, wherein the organic radicals $R_1$ and $R_2$ in the formulae (I) to (IV) are alkyl, cycloalkyl, aryl, arylalkyl or alkyl-aryl radicals.

3. The process according to claim 2, wherein the organic radicals $R_1$ and $R_2$ have from 2 to 10 carbon atoms.

4. The process according to claim 1, wherein the organic radicals $R_1$ and $R_2$ are methyl, ethyl, propyl, n-butyl, isopropyl, isobutyl, n-hexyl, cyclohexyl, methylcyclohexyl, phenyl, benzyl, ethylphenyl, phenylethyl or xylyl.

5. The process according to claim 1, wherein the metals belonging to groups 2 to 14 of the periodic system are selected from the group consisting of titanium, vanadium, chromium, iron, cobalt, nickel, copper, silver, zirconium, niobium, neodymium, dysprosium, gadolinium, samarium, praseodymium and uranium.

6. The process according to claim 1, wherein the neutral ligand $L_1$ is selected from the group consisting of neutral molecular which bind to the metal M with a co-ordination bond without jeopardizing the stability of the carbamate itself.

7. The process according to claim 6, wherein the neutral ligand $L_1$ is an amine or an organic nitrile.

8. The process according to claim 1, wherein the anionic ligand $L_2^{m-}$ is selected from the group consisting of halides, nitrates, sulfites and acetates.

9. The process according to claim 8, wherein the anionic ligand $L_2^{m-}$ is selected from the group consisting of halides, sulfates and acetates.

10. The process according to claim 1, wherein the metal salts are salts of metals formed from mineral acids or organic acids.

11. The process according to claim 10, wherein the mineral acids are selected form the group consisting of halides, sulfates and phosphates.

12. The process according to claim 11, wherein the organic acids are selected from the group consisting of acetates, formates and propionates.

13. The process according to claim 10, wherein the metal salts are selected from the group consisting of titanium chloride ($TiCl_3$), chromium chloride ($CrCl_2$), ferrous chloride ($FeCl_2$), ferric chloride ($FeCl_3$), cobalt ($CoCl_2$), nickel chloride ($NiCl_2$), copper acetate ($Cu(CH_3COO)_2$), $LnCl_3$ wherein Ln represents a lanthanide metal with an atomic number of between 57 and 71 and $AcCl_4$ wherein Ac represents an actinide metal with an atomic number of between 89 and 103 or their hydrate forms.

14. The process according to claim 13, wherein the lanthanide is neodymium or praseodymium.

15. The process according to claim 13, wherein the actinide is thorium or uranium.

16. The process according to claim 1, wherein the aprotic solvent is selected from the group consisting of aliphatic hydrocarbons, chlorinated aliphatic hydrocarbons, aromatic hydrocarbons, ethers and mixtures of two or more of the above solvents.

17. The process according to claim 16, wherein the aliphatic hydrocarbons are selected from the group consisting of pentane, hexane, octane and decane.

18. The process according to claim 17, wherein the aliphatic hydrocarbon is hexane.

19. The process according to claim 16, wherein the chlorinated aliphatic hydrocarbon is methylene chloride.

20. The process according to claim 16, wherein the aromatic hydrocarbons are benzene or toluene.

21. The process according to claim 16, wherein the ether is diethyl ether.

22. The process according to claim 1, wherein the secondary amines having the formula (V) are selected from the group consisting of diethylamine, di-n-propylamine, di-isopropylamine, di-n-butylamine, di-sec-butyl-amine, di-n-pentylamine, di-n-hexylamine and di-cyclohexylamine.

23. The process according to claim 22, wherein the amines are select from the group consisting of di-n-propylamine and di-n-butylamine.

24. The process according to any of the previous claims, wherein the water solution of the metal salt is prepared at a concentration of between about $10^{-2}M$ and $10^1M$.

25. The process according to claim 24, wherein the water solution of the metal salt is prepared at a concentration of between about $10^{-1}M$ and $1M$.

26. The process according to claim 1, wherein the water solution of the metal salt is brought to a temperature of between about $-5°$ C. and $+25°$ C.

27. The process according to claim 26, wherein the water solution of the metal salt is brought to a temperature of about $0°$ C.

28. The process according to claim 7, wherein the solution of the secondary amine having the formula (V) in the aprotic solvent is prepared at a concentration of between about $10^{-1}M$ and $1M$.

29. The process according to claim 1, wherein the solution of the secondary amine having the formula (V) in the aprotic solvent is brought to a temperature of between about $-15°$ C. and $+25°$ C.

30. The process according to claim 29, wherein the solution of the secondary amine having the formula (V) in the aprotic solvent is brought to a temperature of between about $-15°$ C. and $0°$ C.

31. The process according to claim 1, wherein the solution of the secondary amine having the formula (V) in the aprotic solvent is saturated with carbon dioxide.

32. The process according to claim 1, wherein the water solution of the metal salt is added to the solution of the secondary amine having the formula (V) in the aprotic solvent saturated with carbon dioxide.

33. The process according to claim 32, wherein the two solutions are maintained in contact, under light stirring, for a time of between a few minutes and several days, at a temperature of between about $-15°$ C. and $+25°$ C.

34. The process according to claim 33, wherein the two solutions are maintained in contact, under light stirring, for a time of between a few minutes and several days, at a temperature of between about $-15°$ C. and $0°$ C.

35. The process according to claim 1, wherein the molar ratio between the metal salt and the amine used in the reaction is between about 2 and 15.

36. A method of effecting polymerization of one or more unsaturated monomers, which comprises effecting said polymerization in the presence of a solution of the N-alkyl substituted metal carbamate of claim 1.

37. The method of claim 36, wherein the one or more unsaturated monomers are olefinic monomers or diolefinic monomers.

38. The method of claim 37, wherein the olefinic monomers are selected from the group consisting of ethylene, propylene, butene-1, hexene, octene and styrene.

39. The method of claim 36, wherein the diolefinic monomers are selected from the group consisting of butadiene, isoprene, and 1,3-pentadiene.

* * * * *